United States Patent [19]

Grice, Jr.

[11] 3,984,895

[45] Oct. 12, 1976

[54] DENSITY SENSING AND CONTROLLING EQUIPMENT

[75] Inventor: Karl R. Grice, Jr., Honea Path, S.C.

[73] Assignee: Fiber Controls Corporation, Gastonia, N.C.

[22] Filed: Dec. 20, 1974

[21] Appl. No.: 534,808

Related U.S. Application Data

[63] Continuation of Ser. No. 411,841, Nov. 1, 1973, abandoned.

[52] U.S. Cl. .................................. 19/240; 73/32 A; 73/67.6; 73/69; 73/160
[51] Int. Cl.² ....................... G01N 9/24; D01H 5/38
[58] Field of Search ............. 73/32 A, 67.5 R, 67.6, 73/69, 160; 19/98, 150, 240, 288

[56] References Cited
UNITED STATES PATENTS

| 2,843,882 | 7/1958 | Lewis et al. | 19/240 |
| 2,966,057 | 12/1960 | Heller | 73/67.6 |
| 3,088,175 | 5/1963 | Aoki | 19/240 |
| 3,470,734 | 10/1969 | Agdur | 73/32 A |
| 3,562,866 | 2/1971 | Roberson et al. | 19/240 |
| 3,822,590 | 7/1974 | Tharpe et al. | 19/240 X |

FOREIGN PATENTS OR APPLICATIONS

| 930,873 | 7/1963 | United Kingdom | 19/240 |
| 710,124 | 6/1954 | United Kingdom | 73/69 |

Primary Examiner—James J. Gill
Attorney, Agent, or Firm—Cushman, Darby & Cushman

[57] ABSTRACT

Apparatus in a card for sensing and controlling the relative speeds of the feed and doffer rolls in accordance with the sliver density as sensed by error detection circuitry responding to the amount of a transduced compression wave in the sonic ultrasonic range which passes through the sliver.

18 Claims, 7 Drawing Figures

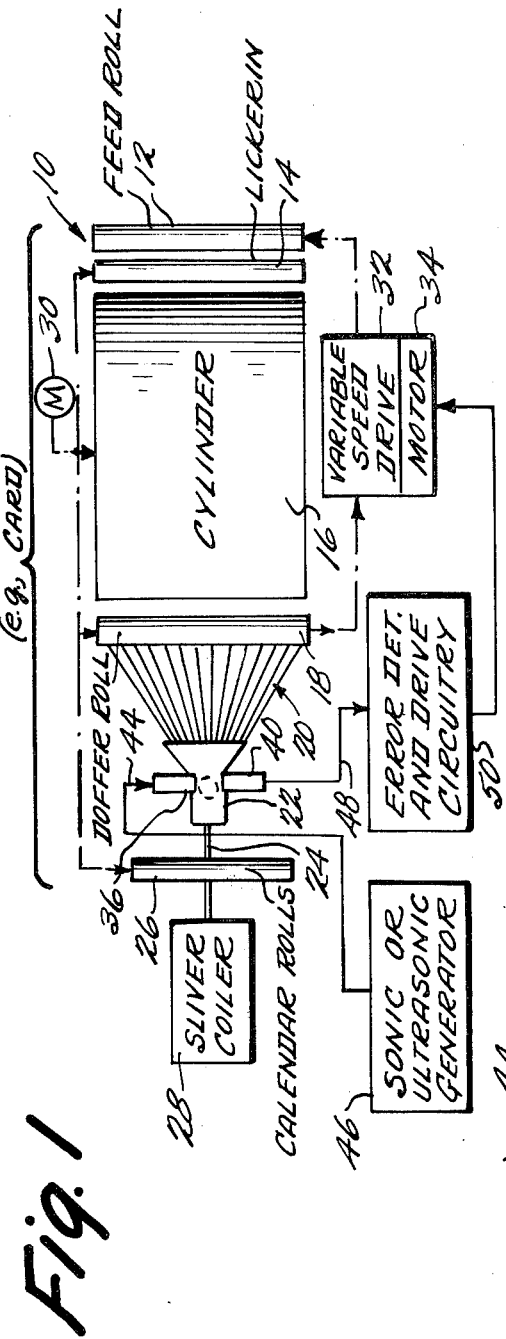
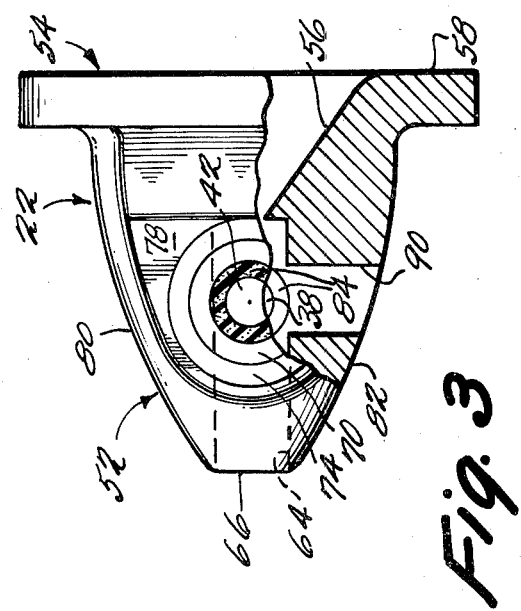
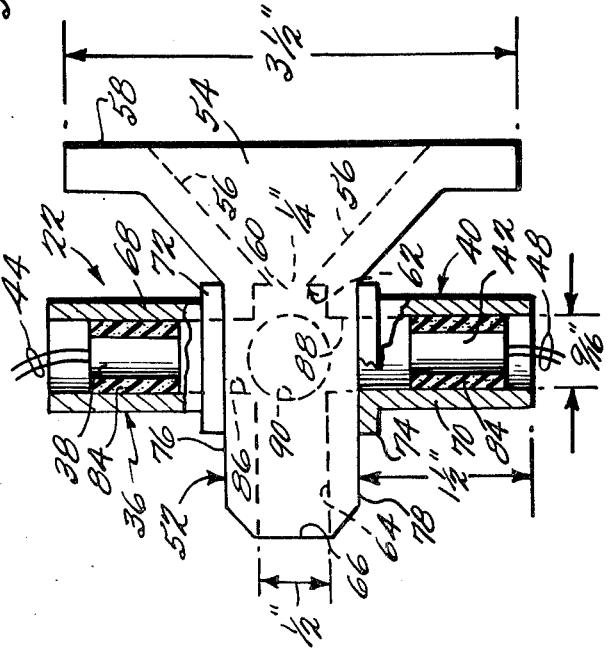

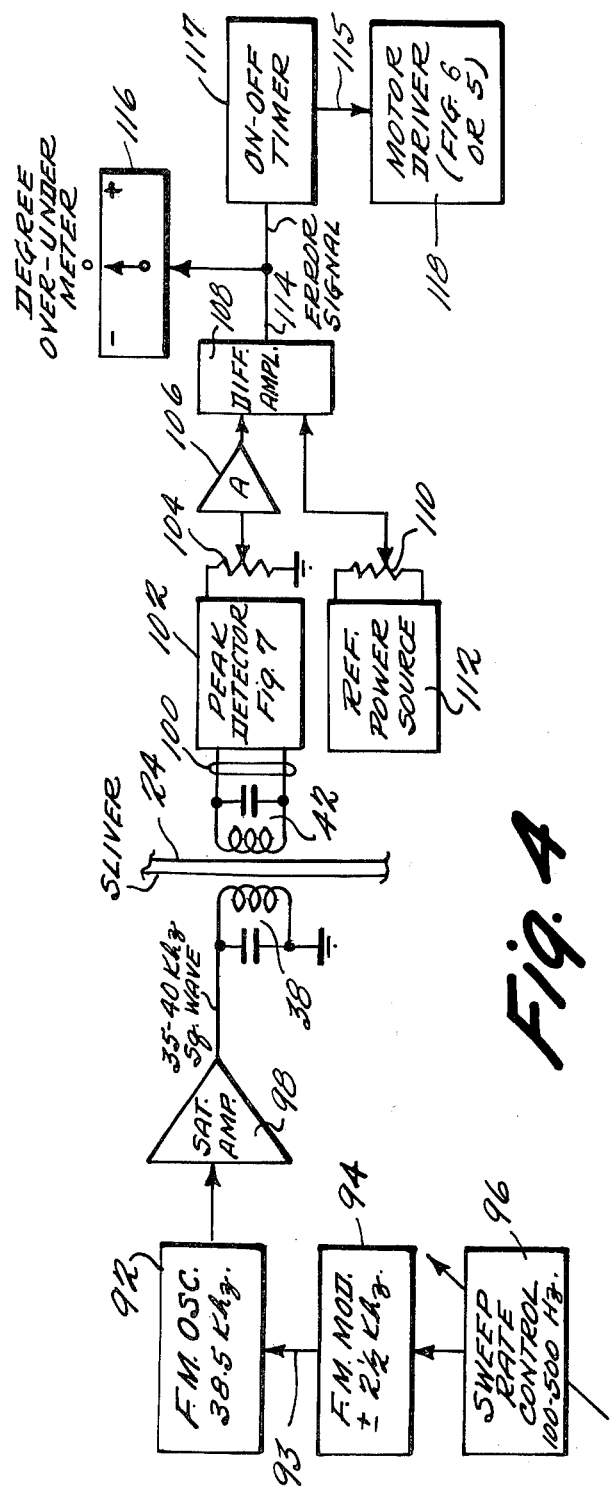
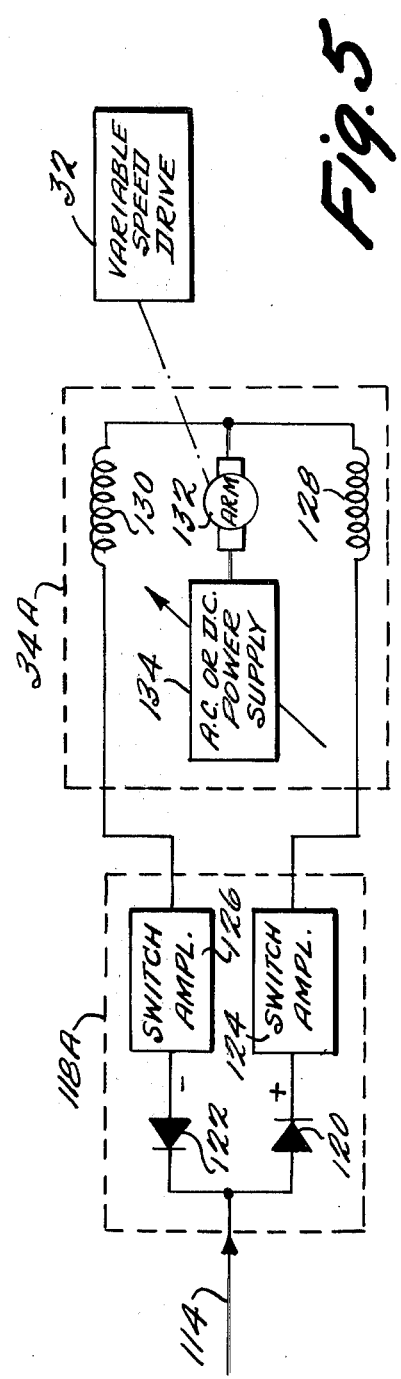
Fig. 4
Fig. 5

DENSITY SENSING AND CONTROLLING EQUIPMENT

This is a continuation of my copending application Ser. No. 411,841, filed Nov. 1, 1973, now abandoned.

BACKGROUND

This invention relates to the sensing of the density of rod-like material and to the controlling of the density thereof, and especially in the field of textile fibers this invention particularly relates to sensing the density of slivers produced by textile machines and to the controlling of the sliver density by controlling the input speed of the machine.

While the invention is particularly described below relative to a carding machine or card, it will be appreciated that the invention extends to other types of textile processing equipment, such as drawframes and pin drafters, which also produce slivers.

As above indicated, besides relating to the sensing to sliver density, this invention also relates to the controlling of that density, i.e., to the automatic leveling of the density of the sliver produced by a textile machine or to rod-like material produced by other machines such as cigarette making machines. Automatic sliver leveling equipment for cards and other textile machines and machines in other fields are in general well known and are frequently referred to as "autolevelers". For example, the Zellweger Ltd. company of Uster, Switzerland advertises a card sliver leveling device under the name "Uster's Control Card System", with an indication that sliver weight never exceeds ± 2%. Used in such systems to measure the cross section of the sliver is a pneumatic sensing trumpet or funnel-shaped nozzle such as shown in the Uster British Pat. No. 1,137,297 and also in U.S. Pat. No. 3,435,673 granted Apr. 1, 1969. Those patents review many of the prior art ways of sensing variation in the substance cross-section of textile material, slivers in particular, and of course describe in detail the Uster pneumatic way of measuring sliver cross-sections. Cross-sectional measurement by such prior art does in fact appear to measure sliver density effectively, or sliver weight if the thickness is held uniform. For reasons stated in those patents, the various measuring systems prior to the pneumatic measuring system have disadvantages and obviously so does the latter, which it is an object of the present invention to obviate. In particular, the present invention measures the density of a sliver or other rod-like material by employing compression waves in the sonic or ultrasonic range of frequencies, in order to secure an improved sensing of the density variations which may occur therein.

Use of sonic and ultrasonic beams or waves to sense the density of a fiber mass has heretofore been used by the assignee hereof, for example, as shown in the Lytton et al U.S. Pat. No. 3,158,291, in a card feeder for purposes of controlling the density and thickness of the web produced by that feeder. In addition, others have employed variable speed drives between the doffer and feed rolls in cards, and have controlled therewith the input speed of the feed roll in response to the sensing of the sliver cross-section, thickness or density by the various ways discussed above. However, to applicant's knowledge, no one heretofore has employed sonic or ultrasonic waves in the manner herein described below in detail to sense the density of slivers or to control the density thereof. Hence, such is the object of this invention in the detail to which the claims define the scope of the invention, which is first described in detail below in reference to the drawings, wherein:

BRIEF DESCRIPTION OF THE DRAWINGS

FIG. 1 shows a diagrammatic top view of a card type of sliver producing textile machine including the invention hereof, FIG. 2 shows a plan view, partially in cross section, of the novel sonic ultrasonic sliver density sensing trumpet, FIG. 3 is a side elevational view of the trumpet of FIG. 2, partially broken away, FIG. 4 is a block diagram of novel circuitry for deriving an error signal representing deviation of the sliver density from a norm, FIG. 5 shows one embodiment of the motor driver of FIG. 4 and of one type of motor for operating the variable speed drive.

DETAILED DESCRIPTION OF THE DRAWINGS

Figure 6:
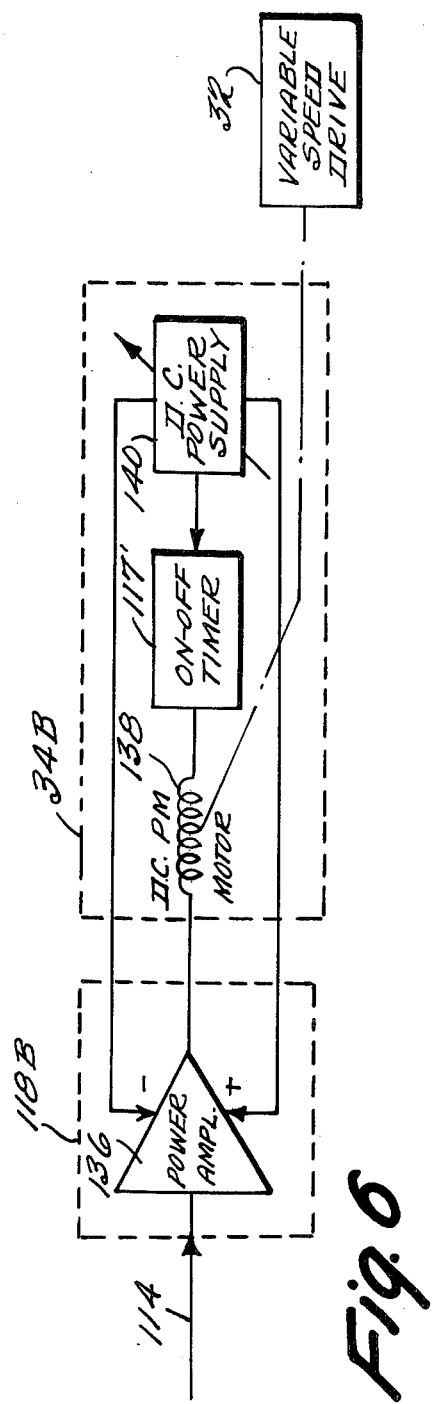
FIG. 6 shows another embodiment of the FIG. 4 motor driver and a different type of motor arrangement for operating the variable speed drive, and FIG. 7 details one embodiment of the peak detector of FIG. 4.

In FIG. 1 the textile fiber processing machine is diagramatically indicated as a carding machine or card 10, which may be of any well known type in general, with the usual feed roll 12, lickerin 14, the large fiber paralleling cylinder 16, and a doffer roll 18. As is well known roll 18 doffs cylinder 16 to remove therefrom a fine web of parallel strands. These strands are brought together as a web 20 by a novel collecting device 22 to produce therein sliver 24 which is pulled through the collector device 22 by conventional calendar rolls 26 and the sliver is coiled in the usual manner by coiler 28.

As is also conventional, an electric motor 30 drives the cylinder 16, lickerin 14 and the doffer and calendar rolls 18 and 26 in the usual manner, but the feed roll 12 is driven by the doffer roll through a variable speed drive 32 to which there is connected an electric motor 34. The variable speed drive 32 is preferably of the type which combines infinitely variable speed control with positive power transmission, e.g., the PIV type supplied by the Link-Belt Enclosed Drive Division of the FMC Corporation, such as shown in their book 3074 078(2), especially the electric remote control models thereof shown and described on pages 46 and 47 of that book. These latter variable speed drives therefore include motor 34 of FIG. 1.

As above indicated, the fine web 20 in FIG. 1 is collected into a sliver by a novel device 22, which itself is shown in one form in FIGS. 2 and 3. Before describing this collecting device in detail it will first just be noted that one arm 36 of the device contains a transmitting transducer 38, while the opposite arm 40 contains a receiving transducer 42. As indicated in FIG. 1 the transmitting transducer receives over line 44 an electrical signal from generator 46 which produces frequencies in the sonic or ultrasonic range. Transducer 38 then changes those electrical signals into a transverse compression wave which has no electrical field or magnetic field, i.e., is in the sonic or ultrasonic frequency range, and that compression wave is transmitted by a transducer 38 toward the receiving transducer 42. If no sliver is passing through the device 22, then the receiving transducer 42 receives the full amount of the compression wave, but on the other hand if the sliver is present in the collecting device 22 then the compression wave is attenuated in accordance with the density of the sliver, and the receiving transducer 42 consequently receives less of the compression wave. The part of the compression wave that it does receive is transduced into a corresponding electrical signal on line 48, which as shown in FIG. 1 leads to error detecting and drive circuitry 50, the output of which operates motor 34, to cause it to rotate in a forward or reverse direction, and consequently to vary the speed of the variable speed drive 32 in known manner. The error detecting circuitry in one form may be like that in the aforementioned Lytton et al. patent. Varying the speed of drive 32 in turn causes the feed roll 12 to increase or decrease its speed relative to doffer roll 18 as well as the other components driven by motor 30. As will be discussed in more detail below relative to FIGS. 5 and 6, the forward or reverse speed of motor 34 may be constant, or alternatively it may be at a rate proportional to the error signal detected by circuitry 50, which is detailed in FIG. 4.

Before discussing the details of FIGS. 4, however, FIGS. 2 and 3 are again considered for purposes of describing the strand collector and sliver producing device 22. Overall, it has generally a funnel shape with the previously mentioned arms 36 and 40 on opposite sides of the rearward or downstream tube-like section 52. Its front or receiving end 54 is cone shaped at least internally and generally also externally as shown in the plan view of FIG. 2. The inside conical surface 56 is quite widespread and has an angle of at least about 120° so as to receive all of the strands of web 20 of FIG. 1 without too great an angle problem, as is conventional. Conical surface 56 at its exterior edge smoothly merges into an outer rim 58 which may have an exemplory diameter of 3½ inches. At its inner end, conical surface 56 reduces to a constricted opening 60 having an exemplory diameter of 174 inch. That opening immediately widens by virtue of shoulder 62 into a constant diameter opening of approximately twice that of aperture 60, i.e., the sliver throughput aperture 64 is preferably approximately ½ inch in diameter. This aperture extends all the way through tube section 52, which has an exit opening 66 from which the sliver 24 in FIG. 1 is withdrawn at a constant speed by calendar rolls 26.

Arms 36 and 40 in FIG. 2 include respectively tube sections 68 and 70 which have respective collars 72 and 74 that are affixed to opposite sides 76 and 78 in any desired manner. It will be noted that these sides 76 and 78 of tube section 52 are flat for this purpose, as opposed to their adjacent top side 80 and bottom side 82 shown in FIG. 3, which are more arcuate and merge smoothly with the exterior top and bottom of the front section 54.

As previously mentioned, the side arms 36 and 40 in FIG. 2 carry the transmitting transducer 38 and receiving transducer 42 respectively. These transducers are securely positioned within tubes 68 and 70 by a respective foam rubber cushion 84 which encircles the transducers. The interior aperture of tubes 68 and 70 has a diameter in the area of 9/16 inch and the inner ends of these apertures communicate with the sliver throughput aperture 64 by virtue of the transverse apertures 86 and 88, which are in alignment with each other. This causes the transmitting and receiving transducers 38 and 42 to be in alignment also, and allows any sliver in the throuput aperture 64 to be struck by the compression wave from the transmitting transducer 38 so that any part of that wave which passes through the sliver is consequently received by the receiving transducer 42.

The constricted opening 60 at the beginning of the wider throughput aperture 64 causes the strands connected by the receiving end 54 to be collected into the form of a sliver which then generally maintains a uniform diameter at least while it passes through the compression wave. In other words, the thickness of the sliver as it passes through the compression wave remains substantially constant, so generally it is the weight of the sliver that is being detected, though in a generic sense it is the density thereof. In order to relieve any air pressure built up inside the throughput aperture 64 by the passing of the sliver therethrough, that aperture is vented exteriorly in the area of the compression wave by a vertically oriented opening or port 90 which as shown in FIG. 3 preferably extends downward, though it could extend upwardly if desired.

In FIG. 4, the transmitting transducer 38 and receiving transducer 42 are schematically illustrated by a parallel coil and condenser arrangement, with sliver 24 passing through them. These transducers are those shown in FIG. 2, and for convenience the rest of the mechanical details of FIG. 2 are omitted from FIG. 4. It should be understood that each of the transducers may be just a piezoelectric crystal respectively or that they may each in fact be a coil with a parallel condenser. In any event, the transducers 38 and 42 are operative as resonant circuits, but as is more apparent below they need not be perfectly matched as to frequency. For purposes of discussion, it will be assumed that the resonant frequency of transmitting transducer 38 is 38.5 KHz., but as previously indicated this invention is operable at least with any sonic or ultrasonic frequency and can even use higher frequencies as long as the sliver absorption factor is not too great so as to prevent a useful output signal to the receiving transducer for measurement purposes. Generally, sonic frequencies generally range downward from 20 KHz., while ultrasonic frequencies are generally considered in the 20 KHz. to 100 KHz. range.

In order to increase the stability of the operation of the system, particularly to prevent false outputs in weight or density changes that are due to temperature changes or changes in some other factor than density itself, the distance between the transducers must be held constant, which is obviously accomplished by the structure in FIG. 2. Preferably, the distance between the facing faces of the transducers is between 2 inches and 12 inches. The distance is sufficient in any event, to prevent change in amplitude of the output signal from the receiver transducer if by chance the face to face transducer distance changes, but at the same time the distance therebetween needs to be close enough to ensure absorption by the sliver while still allowing a sufficient amount of the compression wave to be detected and used in determining density deviation.

Stability of the FIG. 4 system is also promoted by supplying the transmitting transducer 38 with a frequency modulated square wave which is swept between a lower frequency and a higher frequency at some low frequency rate. In the example given, an FM oscillator 92, operating at a frequency of 38.5 KHz., is modulated by ± 2½ KHz. on output line 93 from FM modulator 94 and control device 96 sweeps the oscillator 92 between 35 and 40 KHz at a preset rate in the range of 100–500

Hz., for example. The output of oscillator 92 is then applied to a squaring device such as a saturated driving amplifier 98. This amplifier consequently provides a constant amplitude, variable frequency square wave signal to transducer 38. Such a square wave is obtained regardless of whether the FM signal in oscillator 92 is modulated by a triangular or sine wave, though the latter may be better becuase its top level effectively lasts longer per cycle. Use of frequency modulation and a saturated amplifier 98 not only prevents amplitude instability in the system but allows for some mis-match in the resonant frequencies of the transmitting and receiving transducers 38 and 42. That is, the sweeping of the square wave signal from 35 to 40 KHz., allows the transmitting transducer 38 to be resonant at any frequency within that range, and likewise for the receiving transducer 42 even if the respective center resonant frequencies of the two transducers are different. Transducer 42 does not need to have the same center frequency as transmitting transducer 38, since in any event a peak will occur across the output lines 100 from the receiving transducer 42, and peak detector 102 is insensitive to a sufficient degree to detect peaks regardless of what the resonant frequency is of transducer 42, as long as it is within the 35 to 40 KHz band of frequencies applied to the transmitting transducer 38. This will become more apparent from the discussion later below relative to the description of the peak detector details in FIG. 7.

Applying square waves to the transmitting transducer 38 in FIG. 4 provides for a greater peak power output level from the system, and the desired amount of power supplied to the ultimate load may be regulated by varying the arm on potentiometer 104, the output of which is applied through an amplifier 106 to a different amplifier 108 at one input, the other input of which is from another potentiometer 110. This latter potentiometer is connected across a reference power source 112. Preferably, this power source has a temperature coefficient of ±0.0005%/C°, and preferably the potentiometer 110 has a temperature coefficient which also makes it quite stable, for example in the area of 25 parts per million per ° C. The arm of potentiometer 110 is employed to set into the system the desired or normal grain weight required for the sliver being produced by the card 10 in FIG. 1. For example, this setting may be in the range of 50 to 80 grains, and it will be appreciated that since this setting is the reference or null which is compared in difference amplifier 108, the stability of the whole system depends upon the stability of the reference voltage selected by the arm of potentiometer 110. Changes in that voltage by other than movement of the potentiometer arm, can obviously cause false grain weight indications, since the error signal produced on the output line 114 from difference amplifier 108 will itself be erroneous and cause an erroneous indication on meter 116 and an erroneous operation of motor driver 118, which in turn will cause a false correction of the operation of motor 34 in FIG. 1 and of the variable speed drive 32 and consequently of the feeding by feed roll 12. On the other hand, with the desired stability built into the reference power source 112 and potentiometer, 110, difference amplifier 108 will provide a correct error signal on line 114. This error signal is a DC signal which is either more or less than zero, i.e., plus or minus, if not zero itself. The amplitude of the error signal indicates the degree that the sliver 24 has deviated from the norm, and this may be appropriately shown on the over-under meter 116, if desired. The same error signal on line 114 may be employed if desired to control the sliver density in the manner previously discussed relative to FIG. 1, by applying it to motor driver 118.

As shown in FIG. 5, one embodiment of such a motor driver is designated 118A, which includes a drive splitter or polarity divider including oppositely oriented diodes 120 and 122 which respectively operate on-off switching amplifier drivers 124 and 126 by the respective positive and negative signals received thereby. Amplifiers 124 and 126 may be, for example, conventional thyristors or Triacs, which are well known in the art. The output of switch amplifiers 124 and 126 are applied to motor 34A, which is one embodiment of either an AC or DC motor corresponding to motor 34 in FIG. 1. In FIG. 5, motor 34A has two field winding 128 and 130 which are respectively connected to the outputs of switch amplifiers 124 and 126, with the opposite ends of the field windings being connected together to the armature 132 on one side, the other side of which is connected to an AC or DC variable power supply 134. When the DC error signal on input line 114 is positive so as to turn on switch amplifier 124, field winding 128 is energized to cause armature 132 to rotate in one direction, for example, the forward direction, which causes the speed of the variable speed drive 32 to increase, thereby causing the feed roll 12 in FIG. 1 to increase its speed in an effort to reduce the lightness of the sliver density back toward the norm or reference preset by potentiometer 110 in FIG. 4. While motor 34A has a power supply 134 in FIG. 5 that is variable and which in fact sets the speed of the armature, the motor driver 118A does not provide for proportional speed control of the variable speed drive. That is, the change in speed of the variable speed drive 32 is not proportional to the amplitude of the error signal on line 114. Instead, motor 34A is just operated in a forward direction or a reverse direction at a speed predetermined by the setting of power supply 134. Consequently, an increase in the speed of feed roll 12 as effected by motor 34A in FIG. 5, may well cause the density of the sliver 24 produced by the card to over shoot its norm, in which case the diode 122 in FIG. 5 would pass a negative signal to turn on switch amplifier 126, causing the motor to operate in the reverse direction so as to cause the variable speed drive in turn to reduce the speed of the feed roll 12 in FIG. 1. This kind of continuous operation may well cause "hunting" of the equipment so that the long term density of the sliver may continuously increase and decrease and never stay level at zero deviation from the reference or norm set by potentiometer 110 in FIG. 4. In an effort to relieve hunting, the on-off timer 117 in FIG. 4 may be employed so that the error signal on line 114 is applied to the motor driver 118 for only a given time and then turned off for another given time. For example, timer 117 could operate to turn on the motor driver for 10 seconds and the turn it off then for another 10 seconds, and to continuously repeat that cycle, thereby preventing over correction of the sliver density and making it possible to actually level the density with zero error to the norm preset by potentiometer arm 110.

FIG. 6 illustrates another alternative motor driver 118B used in conjunction with another alternative type motor 34B. In particular, since the error signal on line 114 in FIG. 4 is a DC signal, the polarity splitter in driver 118A of FIG. 5 can be eliminated and instead the error signal can be applied directly to a power amplifier 136, which will operate on both positive and negative DC input signals in a conventional fashion. Motor 34B is of the DC permanent magnet type with an armature coil 138 connected at one end to the output power amplifier 136 and connected at its other end through an on-off timer 117' if desired to a variable DC power supply 140, the output of which is also applied in both polarities back to the power amplifier 136. Accordingly, the positive or negative DC signal on line 114 causes the motor armature to operate in a forward or reverse direction and at a rate which is proportional to the amplitude of the error signal on input line 114, i.e., proportional to the excess or underage of the grain weight or density relative to the reference set by potentiometer 110 in FIG. 4. Consequently, motor armature 138 drives the variable speed drive not only in the appropriate direction but at a proportional speed to cause feed roll 12 in FIG. 1 to increase or decrease its speed proportionately to the underage or overage respectively, so that the density of the output sliver 24 returns back toward the preset norm. Since this is a proportional control system, the on-off timer 117' may not be necessary, but if it is used, it would be employed in the same manner as discussed above, relatively to timer 117 in FIG. 4, though the on-off times may be different for the FIG. 6 arrangement than needed for the FIG. 5 arrangement. Of course, timer 117' may be completely eliminated if desired, or alternatively, the output from timer 117 in FIG. 4 may be applied to the power amplifier 136 if desired, instead of the error signal that appears on line 114. It should be noted that the error signal on line 115 is the same as that on line 114, as to polarity and amplitude, though it may be turned on and off at various times.

Figure 7:
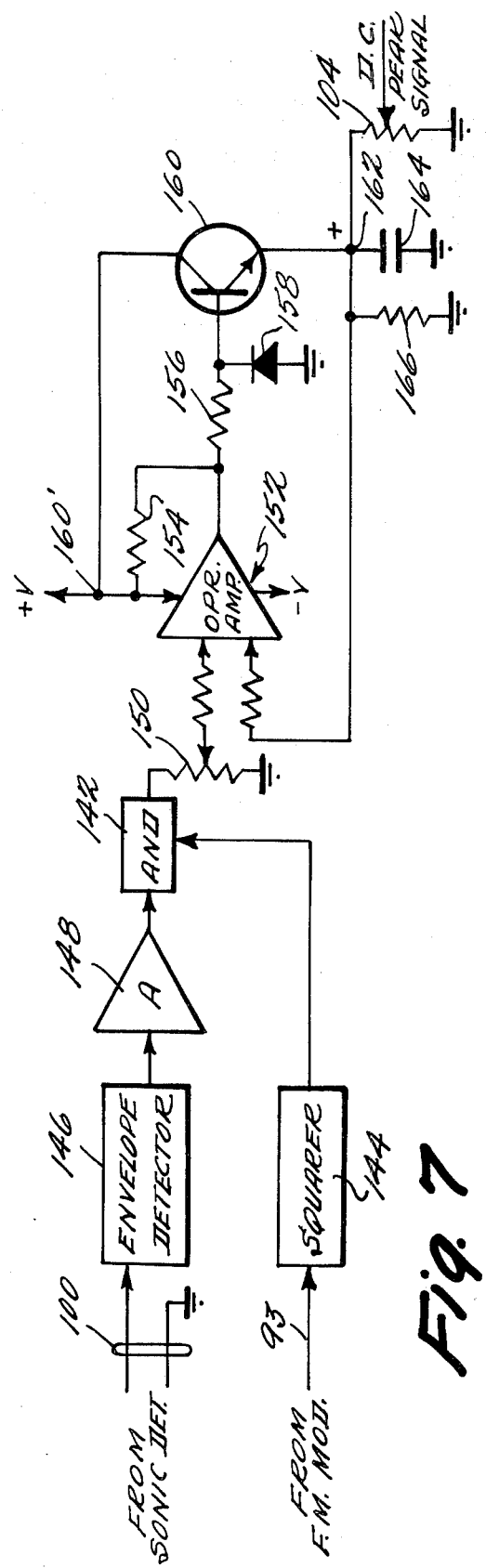

Reference is now made to FIG. 7, which details one embodiment of the peak detector 102 of FIG. 4 and includes an optional AND circuit 142 and squarer 144 which help eliminate possible noise, as explained in more detail below.

In the FIG. 7 peak detector, the receiving transducer signal on input line 100 is applied to a conventional envelope detector 146, the output of which is applied to an amplifier 148 and then as one input of AND circuit 142. As above mentioned, this AND circuit 142 is optional, but if used in conjunction with the output on line 93 of the FM modulator 94 of FIG. 4 so that its ± 2½ KHz., signal appears on line 93 and is squared by circuit 144, which may be a saturated amplifier similar to amplifier 98 in FIG. 4, the two inputs to AND circuit 142 help eliminate possible noise in the circuit. With or without AND circuit 142, the output is applied across potentiometer 150 the arm of which taps off a desired amount of the signal and applies it to one input of an operational amplifier 152, which includes a feedback resistor 154. This operational amplifier applies its output to resistor 156 and across a diode 158 which clips the negative peaks of the operational amplifier signal. The resulting signal is applied to the base of transistor 160, the collector of which is connected to a positive voltage at terminal 160', which also connects to the operational amplifier in normal fashion. Transistor 160 is operated as a current amplifier, and its emitter output is applied via terminal 162 across condenser 164. This condenser is paralleled by a resistor 166 and the resultant voltage across the condenser and resistor is applied as a feedback input to operational amplifier 152. In this manner, the rapid charge of condenser 164 is fed back to the amplifier to increase its gain and to keep up the fast charging of condenser 164. The RC time constant of resistor 166 and condenser 164 is such as to drain the peaks from the condenser but due to the rapid recharge thereof the condenser and hence terminal 162 carry a DC voltage representing the detected peaks of the receiving transducer output signal. This DC peak signal is applied across potentiometer 104 in FIG. 7, as in FIG. 4, and the rest of the operation of FIG. 4 is as described previously. It may be noted that the operational amplifier 152 in FIG. 7 operates as a stable high gain amplifier which continuously references itself to ground and is effectively operated as an integrater with rapid feedback.

Though not shown, it should be mentioned that the error signal on line 114 could be tapped off to a too high or too low cutoff tripping relay arrangement or the like to turn off the card, for example card motor 30, whenever the density of the sliver deviates too far from the desired reference or norm preset into the system by potentiometer 110 in FIG. 4. Preferably, such a cut off relay system would have a built-in delay of, say, 5 seconds to prevent false cut offs, and of course the relay system would need to be interlocked so that the card could be turned back on while the sliver is regaining its density tolerance allowed by the cut off relay arrangement.

What is claimed is:
1. Apparatus for sensing the relative density of material which is in rod-like form, comprising:
   tube shaped means forming a throughput aperture for receiving said material,
   means for drawing said material through said aperture constantly in said rod-like form,
   transmitting means including a transmitting transducer disposed on one side of said tube means and exposed to said throughput aperture for transmitting into said material a compression wave in the sonic ultrasonic frequency range,
   a receiving transducer exposed to said throughput aperture for receiving the part of said wave that passes through said material,
   said transmitting means including means for generating and delivering to said transmitting transducer a frequency modulated signal which sweeps between higher and lower frequencies through a predetermined center frequency at a given rate,
   said receiving transducer being resonant at a frequency between said lower and higher frequencies,
   circuit detecting means connected to said receiving transducer for generating a signal relating to the peaks of the output signal from said receiving transducer,
   means for producing a reference signal related to a desired density for said material,
   means for deriving the difference between said reference signal and the output signal of said circuit detecting means to produce an error signal as an indication of the density deviation of said material from said desired density.
2. Apparatus as in claim 1 wherein said means for generating a sweeping frequency modulated signal including:
   an FM oscillator operating at substantially said center frequency,
   an FM modulator for sweeping said oscillator by a predetermined frequency above and below said center frequency to effect said higher and lower frequencies, sweep rate control means for causing said modulator to sweep at said given rate, and means for squaring the output signal from said oscillator.

3. Apparatus as in claim 1 wherein said peak detecting circuit means includes:

an envelope detector connected to said receiving transducer, an operational amplifier coupled at a first input to the output of said envelope detector, a current amplifier coupled to the output of said operational amplifier, a parallel RC circuit connected to the output of said current amplifier for producing across the RC circuit the effective peak DC signal value of the detected envelope signal from said envelope detecting means, and means feeding said peak DC value signal from said RC circuit back into said operational amplifier at a second input thereof to maintain a high gain operation of said operational amplifier whereby the RC circuit is rapidly charged and said peak DC signal thereacross is maintained even though the time constant of said RC circuit causes the peaks thereacross to be drained but allows the detected peaks to be followed by the peak DC value signal across the said RC circuit.

4. Apparatus as in claim 3 wherein said modulated generating means includes an FM modulator, and wherein there is provided means for aiding in elimination of possible noise in the system including:

means for squaring the output of said FM modulator, and means for ANDING the output of said squaring means with the output of said envelope detecting means to provide the signal to said first input of said operational amplifier.

5. Apparatus as in claim 1 including:

a machine including said tube means for processing said material into said rod-like form and having material operating means with input feed means and output means for feeding said tube means, means for driving said output means and said drawing means at a given speed, variable speed drive means between said output means and input feed means, motor means for operating said variable speed drive means, and motor driving means responsive to said error signal for driving said motor means to vary the speed of said input feed means via said variable speed drive in a direction to reduce said error signal toward zero.

6. Apparatus as in claim 5 wherein said motor driving means includes respective polarity deriving means for separating said error signal into plus and minus signals for indicating that the density is over or under the said predetermined density, and wherein said motor has two field coils that respectively receive said plus and minus signals to cause operation of the said variable speed drive means in the direction to reduce the error signal as aforesaid.

7. Apparatus as in claim 6 wherein said motor driving means further includes between each said motor coils and the respective polarity deriving means a respective on-off switching amplifier.

8. Apparatus as in claim 6 wherein said motor means has an electrical armature and includes a variable power supply for said armature to control the basic forward and reverse speeds of said motor means.

9. Apparatus as in claim 5 wherein said motor means includes a direct current permanent magnet motor having an armature coil, and said motor driving means includes a power amplifier connected to receive said error signal and providing an output to one side of said armature coil, and power supply means connected to the other side thereof and providing both plus and minus signals to said power amplifier to cause the motor means and hence said input feed means to be operated at a rate proportional to the amplitude of said error signal and in a forward or reverse direction according to the polarity of said error signal.

10. Apparatus as in claim 1 wherein said frequency modulated signal is a square wave signal.

11. Apparatus as in claim 1 wherein said receiving transducer is disposed on the side of said tube means opposite to said one side.

12. Apparatus for sensing the relative density of material which is in rod-like form, comprising:

means for receiving said material, means for drawing said material through said receiving means constantly in said rod-like form, transducer means adjacent said receiving means for producing an electrical output signal varying in relation to the relative density of said material, circuit detecting means connected to said transducer means for generating a signal relating to a unique characteristic of said electrical output signal from said transducer means, means for producing a reference signal related to a desired density for said material, and means for deriving the difference between said reference signal and the output signal of said circuit detecting means to produce an error signal as an indication of the density deviation of said rod-like material from said desired density, wherein said detecting circuit means includes:

an envelope detector connected to said transducer means, an operational amplifier coupled at a first input to the output of said envelope detector, a current amplifier coupled to the output of said operational amplifier, a parallel RC circuit connected to the output of said current amplifier for producing across the RC circuit the effective peak DC signal value of the detected envelope signal from said envelope detecting means, and means feeding said peak DC value signal from said RC circuit back into said operational amplifier at a second input thereof to maintain a high gain operation of said operational amplifier whereby the RC circuit is rapidly charged and said peak DC signal thereacross is maintained even though the time constant of said RC circuit causes the peaks thereacross to be drained but allows the detected peaks to be followed by the peak DC value signal across the said RC circuit.

13. Apparatus as in claim 12 wherein said transducer means includes an FM modulator, and wherein there is provided means for aiding in elimination of possible noise in the system including:

means for squaring the output of said FM modulator, and means for ANDING the output of said squaring means with the output of said envelope detecting means to provide the signal to said first input of said operational amplifier.

14. Apparatus as in claim 12 including:
a machine including said receiving and drawing means for processing said material into said rod-like form and having material operating means with input feed means and output means for feeding said tube means,
means for driving said output means and said drawing means at a given speed,
variable speed drive means between said output means and input feed means,
motor means for operating said variable speed drive means, and
motor driving means responsive to said error signal for driving said motor means to vary the speed of said input feed means via said variable speed drive in a direction to reduce said error signal toward zero.

15. Apparatus as in claim 14 wherein said motor driving means includes respective polarity deriving means for separating said error signal into plus and minus signals for indicating that the density is over or under the said predetermined density, and wherein said motor has two field coils that respectively receive said plus and minus signals to cause operation of the said variable speed drive means in the direction to reduce the error signal as aforesaid.

16. Apparatus as is claim 15 wherein said motor driving means further includes between each of said motor coils and the respective polarity deriving means a respective on-off switching amplifier.

17. Apparatus as in claim 15 wherein said motor means has an electrical armature and includes a variable power supply for said armature to control the basic forward and reverse speeds of said motor means.

18. Apparatus as in claim 14 wherein said motor means includes a direct current permanent magnet motor having an armature coil, and said motor driving means includes a power amplifier connected to receive said error signal and providing an output to one side of said armature coil, and power supply means connected to the other side thereof and providing both plus and minus signals to said power amplifier to cause the motor means and hence said input feed means to be operated at a rate proportional to the amplitude of said error signal and in a forward or reverse direction according to the polarity of said error signal.

* * * * *